United States Patent

Koetke et al.

[11] Patent Number: 6,056,731
[45] Date of Patent: May 2, 2000

[54] SUCTION DEVICE FOR BODY FLUIDS

[75] Inventors: Claus-Dieter Koetke, Reinstorf/Lueder; Martin Sippel; Volker Klute, both of Melsungen, all of Germany

[73] Assignee: B. Braun Melsungen AG, Melsungen, Germany

[21] Appl. No.: 09/078,569

[22] Filed: May 14, 1998

[30] Foreign Application Priority Data

Jun. 3, 1997 [DE] Germany .......................... 197 23 197

[51] Int. Cl.⁷ .................................................. A61M 1/00
[52] U.S. Cl. ........................................... 604/323; 604/317
[58] Field of Search .................................... 604/317, 319, 604/320, 321, 322, 323, 414, 416; 206/219, 222, 419, 420; 600/573, 575, 578, 579, 580; 137/205, 208, 432, 433; 141/65

[56] References Cited

U.S. PATENT DOCUMENTS

| | | | |
|---|---|---|---|
| 4,384,580 | 5/1983 | Leviton | 604/119 |
| 4,460,361 | 7/1984 | Nichols | 604/319 |
| 4,465,485 | 8/1984 | Kashmer et al. | 604/320 |
| 4,522,623 | 6/1985 | Laiterjung | 604/319 |
| 4,681,571 | 7/1987 | Nehring | 604/320 |
| 5,006,118 | 4/1991 | Yule | 604/408 |
| 5,168,868 | 12/1992 | Hicks | 128/205.12 |
| 5,185,007 | 2/1993 | Middaugh et al. | 604/320 |
| 5,279,602 | 1/1994 | Middaugh et al. | 604/320 |
| 5,363,860 | 11/1994 | Nakao et al. | 128/760 |
| 5,542,939 | 8/1996 | Onodera et al. | 604/319 |
| 5,624,417 | 4/1997 | Cook et al. | 604/319 |
| 5,630,939 | 5/1997 | Bulard et al. | 210/416.1 |
| 5,725,516 | 3/1998 | Cook et al. | 604/319 |

FOREIGN PATENT DOCUMENTS 0390094   3/1990   European Pat. Off. .

*Primary Examiner*—Ronald Stright, Jr.
*Assistant Examiner*—David J. Cho
*Attorney, Agent, or Firm*—Diller, Ramik & Wight, PC

[57] ABSTRACT

A suction device for body fluids comprises a container (10) being airtightly closable by means of a cover (11). A bag (14) is connected to a cylindrical projection (12) of the cover (11) by means of a support ring (13). A suction opening (15) is provided in the cover (11) to produce a low pressure in the bag (14). Furthermore, the suction opening (15) comprises a branching (31) to produce a low pressure in the container (10) as well. Additionally, the cover (11) comprises an outlet opening (17) enclosed by a hollow body (37). The hollow body (37) can be pushed into the container (10) to empty the bag (14) so that the fluid contained in the bag (14) can be poured out via openings (40, 41) of the hollow cylinder (37).

35 Claims, 5 Drawing Sheets

SUCTION DEVICE FOR BODY FLUIDS

BACKGROUND OF THE INVENTION

The invention relates to a suction device for body fluids, especially for use in hospitals.

Suction devices, such as described in EP 0 390 094 A, comprise a solid container in which a flexible bag is inserted. The bag is supported on a cover by means of which the container can be closed in an airtight manner. Furthermore, two connections are provided on the cover, one of which is connectable to the patient and the other to a suction source. Both connections lead towards the interior of the bag. To keep the bag from being completely sucked towards the inside by the suction source so as not to be able to receive any fluid, the container also has to be connected to a suction source. That way, a low pressure is provided both in the bag and in the container so that the shape of the bag is maintained and is able to receive these body fluids.

As soon as the bag is filled with body fluids, these have to be disposed of, for example by being poured into the sewerage. In this context, it has to be taken into consideration that the body fluids are often contaminated, and therefore it has to be avoided that the personnel comes into contact with the fluid. Therefore the closed bags are often disposed of by wet combustion. This process is very expensive and compulsory for suction products from notifiable diseases for reasons of hygiene.

Furthermore, an inspissation substance can be supplied to the body fluid present in the bag to inspissate the fluid. The inspissated fluid can then be dumped or burned as well. The inspissation reduces the risk of contamination of the personnel, as the danger of fluid exiting without control, which cannot be avoided when pouring, is avoided. However, there still is a danger of contamination when supplying the inspissation substance and when taking the bag out of the container, for example when the fluid has not been inspissated completely. Furthermore, the inspissation of body fluids is time-consuming and expensive.

As a third, very expensive way of disposal, the entire container can be disposed of by means of wet combustion.

SUMMARY OF THE INVENTION

It is the object of the invention to provide a suction device for body fluids in which the danger of contamination is avoided even when pouring.

According to the invention, a slide is arranged in an outlet opening of the suction device, which slide is movable rotationally or axially for opening. To open the rotatable slide to supply inspissation substance, the container is supported such that the outlet opening is directed upwards and the slide is rotated by a certain angle. By rotating the slide, openings provided in the slide are aligned with openings provided in the container so that the body fluid present in the container can be inspissated by supplying inspissation substances. In a second possibility of opening the rotatable slide for pouring the fluid, the container, with the slide being closed, is placed upside down or with the outlet opening directed downwards on an opening aid mounted on the bottom of a pouring basin. The opening aid engages the slide so that the outlet opening can be opened by rotating the container. Thus, the rotatable slide for opening does not have to be touched by the personnel, and there is no danger of contamination.

The axially movable slide projects out of the container in the closed position and is pushed into the container in an axial direction for opening. There are also two possibilities to push the slide into the container. In the first possibility, the container is supported such that the outlet opening is directed upwards, such that no body fluid can exit out of the container when the slide is pushed. Then the inspissation substance can be fed into the container. It is not necessary to turn or otherwise unlock the slide before pushing it in. Furthermore, the slide can be pushed in by means of an object so that there is a large distance to the body fluid.

As the slide seals the container in the closing position, the container can be supported for opening, as a second possibility, with the outlet opening directed downwards. In this position, the slide is pressed, for example, against the bottom of the pouring basin or the like, so that the slide is pushed into the container. Standing upside down or with the outlet opening directed downwards, the fluid can be drained from the bag. In this process, the personnel is not required to touch the slide at any point.

Preferably, the rotatable and the axially movable slide are formed as a hollow body closed on the side of the container. The hollow body comprises at least one lateral opening. In the closing position of the rotatable slide, this opening is covered by a projection of the container and is thus closed. In the case of the axially movable slide, this opening is located outside the container or outside the sealing area formed by the area of the hollow body on the side of the container. Furthermore, the hollow body comprises a pouring opening on a side directed away from the container, so that, when the slide is opened, the body fluid flows through the lateral opening into the hollow body and can be poured out of this through the pouring opening. The area of the hollow body on the side of the container can be formed as a guiding body for guiding the fluid and as an additional spray protection. Because of the design of the slide, it serves both to open the outlet opening without any danger of contamination and to improve the pouring capabilities.

Preferably, the axially movable slide in the state of being pushed in terminates on the same level as the two connection pieces of the suction and the inlet opening, so that the container can be supported on these three supports in a stable manner on a plane area. Thus the container can simply be put into a corresponding reception trough to be emptied and does not have to be held by the personnel. In the case of the container with a rotatable slide, the level of the opening aid mounted on the bottom of the basin for opening the rotatable slide is adapted to the slide such that even the container with a rotatable slide is supported firmly on the two connection pieces and the slide and does not have to be supported by the personnel.

As there is a low pressure present in the container and in the bag during the suction process, it has to be ensured, in the case of the axially movable slide, that the slide is not pulled out of its closing position into the container because of the low pressure. This would open the outlet opening of the container so that no low pressure could be produced in the bag any more, and therefore no more body fluid would be sucked off by the suction device. To avoid this, the slide can be turned slightly in the closing position so that it is not possible to open the slide because of low pressure. However, the slide would then have to be turned back before being pushed in.

Therefore, a cap is preferably provided enclosing the slide and forming an airtight seal with the container. If the slide were to be pulled into the container slightly because of the low pressure, a gap between the slide and a corresponding sealing area on the outlet opening would be formed so that a low pressure would also be produced in the cap enclosing the slide. As the cap closes the container in an airtight manner, the same pressure is present on both sides of the slide so that the slide is not pulled into the container any further. Thus, it is ensured in a simple manner that the slide is not pulled into the container because of the low pressure present in the bag.

According to a further development, which is independent, the container is closable in an air-tight manner by means of a cover the bag is fixed to. In the cover, the suction, inlet and outlet openings are provided. According to the invention, the suction opening connected to the bag comprises a branching into the container provided in the cover. Thus, on the one hand, there is a connection into the bag, and on the other hand, there is a connection into the container via the branching. Thus a low pressure is produced by means of the suction source connected to the suction opening both in the bag and in the container. Therefore, it is not required to connect two tubes one of which is connected to the bag and the other of which is connected to the container. Rather, only one tube has to be connected to produce the low pressure in the bag and in the container.

Even in an arrangement of a series of multiple suction devices, only the inlet opening of a subsequent container has to be connected to the suction opening of a preceding container. Apart from that, it is not required to connect each container to the suction source by means of a further tube.

In the case of containers being connected in series, the inlet opening of the first container on the patient's side is connected to the patient, and the suction opening of the last container is connected to the suction source. A hydrophobic filter is arranged in the suction opening of the last container, which closes the suction opening when contacting humidity. Thus it is ensured that no fluid gets into the suction device. The suction openings of the other containers are each provided with a back pressure valve to keep body liquid from flowing into a preceding container.

BRIEF DESCRIPTION OF THE DRAWINGS

A preferred embodiment of the invention will now be described in greater detail with reference to the accompanying drawings.

DESCRIPTION OF THE PREFERRED EMBODIMENTS

Figure 1:
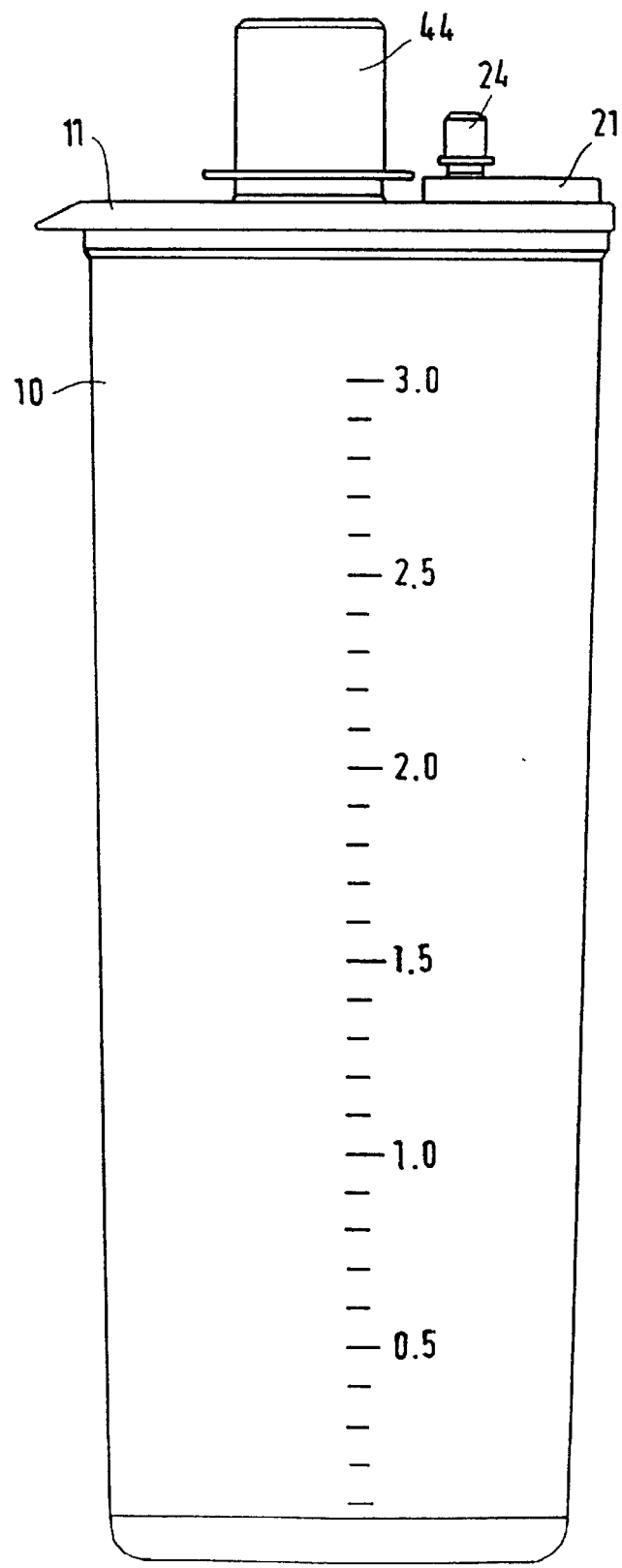
FIG. 1 is a schematic lateral view of a preferred embodiment of a suction device.

The suction device for body fluids comprises a rigid container 10 being closable in an airtight manner by means of a cover 11. The cover 11 comprises a cylindrical projection 12 projecting into the container 10. A flexible bag 14 is fixed to the exterior circumference of the cylindrical projection 12 by means of a supporting ring 13. The bag 14 is thus supported on the cover 11 in a fixed and sealing manner and extends from the cylindrical projection 12 of the cover into the container 10.

Figure 2:
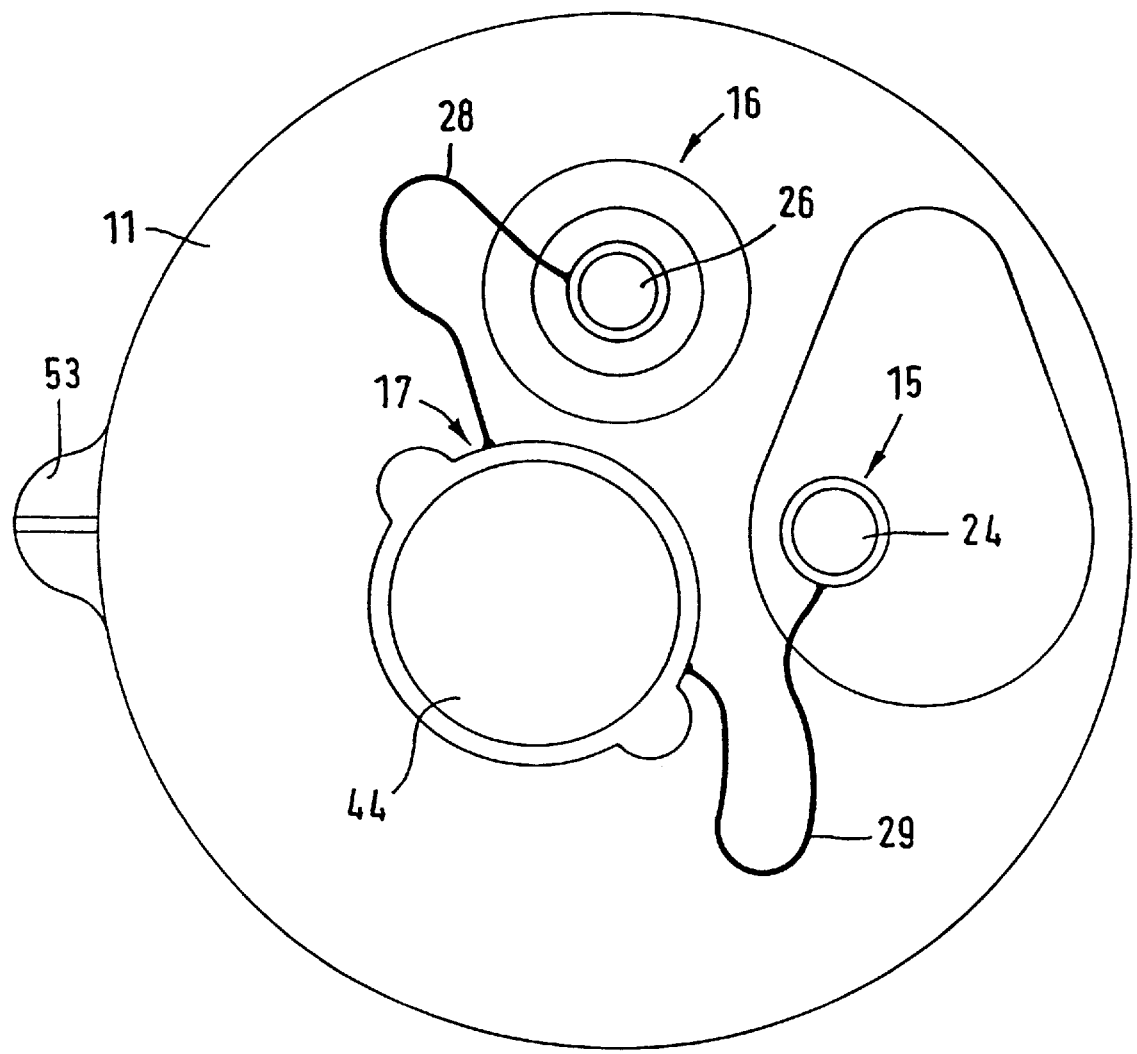
FIG. 2 is a top plan view of the suction device.

In the cover 11, a suction opening 15 is provided being connectable to an external suction source, which is not represented. Furthermore, the cover 11 comprises an inlet opening 16 (FIG. 2) to which a tube from a patient is connectable. The outlet opening 15 and the inlet opening 16 lead into the cylindrical projection 12 of the cover 11 and thus into the bag 14 in which the body fluid sucked off from the patient is collected. Furthermore, an outlet opening 17 is arranged in the cover 11 such that there is a connection to the cylindrical projection 12 and thus to the bag 14. The outlet opening 17 serves to empty the bag 14.

In the area of the suction opening 15, a filter cover 21 is connected to the cover 11 comprising an opening 22 aligned with the suction opening 15 provided in the cover 11. A connection piece 23 is arranged on the cover 21 coaxially with the opening 22, with a closure cap 24 being positionable thereon, for example for transportation purposes. During the operation of the suction device, the closure cap 24 is removed form the connection piece 23, and a tube leading to the suction source is put on the connection piece 23 instead.

Accordingly, the cover 11 comprises a connection piece 25 (FIG. 3) in the area of the inlet opening whereon either a closure cap 26 (FIG. 2) or, during the operation of the suction device, a tube connectable to a patient is attached. The closure caps 24, 26 are attached to the cover 11 by means of tapes 28, 29.

Figure 3:
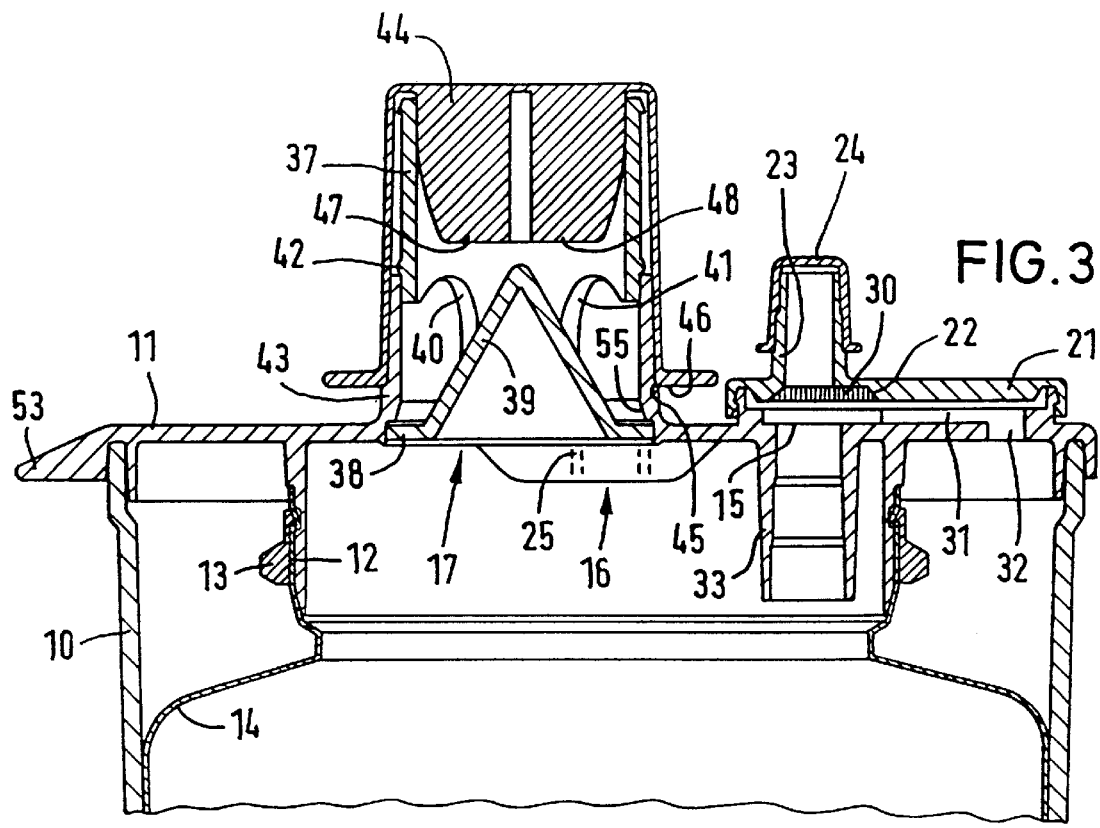
FIG. 3 is a longitudinal cross section of the suction device with an axially movable slide with the outlet opening being closed.

According to FIG. 3, a hydrophobic filter 30 is provided in the opening 22 of the filter cover 21. This filter is permeable to air, but as soon as it gets into contact with humidity, it becomes impermeable to air. In the area of the cover 11 below the filter cover 21, a groove is provided in the cover 11 forming a branching 31 from the suction opening 15 when the filter cover 21 is closed. On the right end of the branching 31 in FIG. 3, an opening 32 is provided in the cover 11 connecting the branching 31 with the interior of the container 10. If a suction source is connected to the connection piece 23 by means of a tube, a low pressure is produced in the bag 14 via the suction opening by sucking air out of the bag via a projection 33 being provided coaxially to the suction opening 15 on the cover 11 and projecting into the cylindrical projection 12 of the cover 11. Simultaneously, air is sucked out of the container 10 surrounding the bag 14 so that approximately the same low pressure is present both in the bag 14 and in the container 10.

Figure 4:
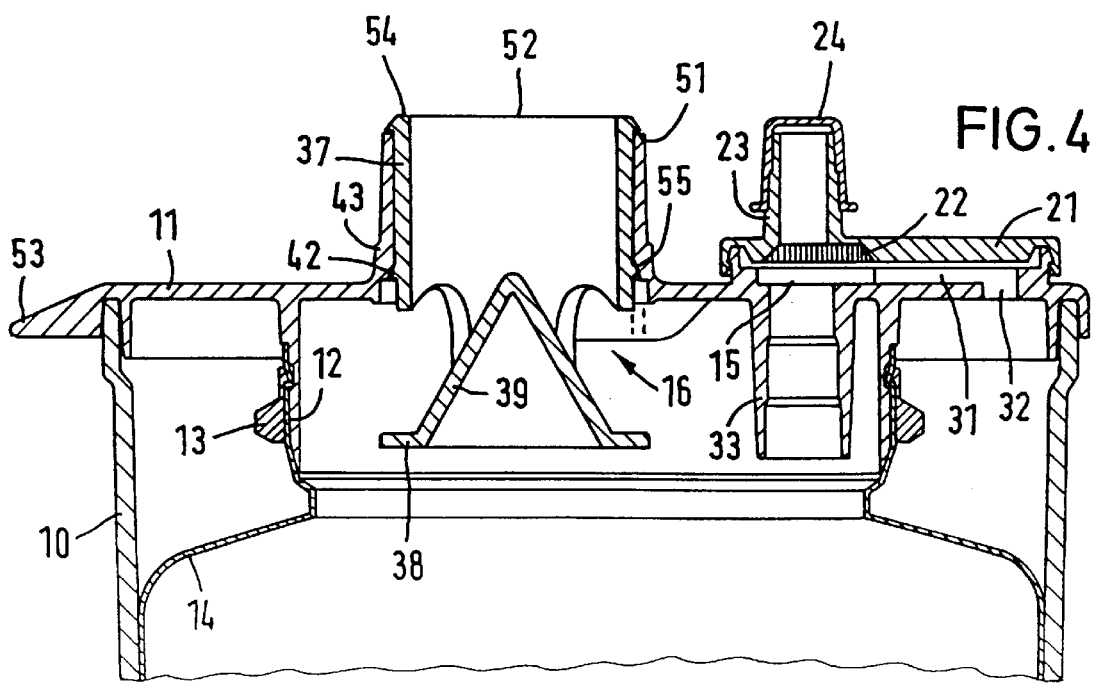
FIG. 4 is a longitudinal cross section of the suction device with an axially movable slide with the outlet opening being opened.

In the embodiment represented in FIGS. 3 and 4, a cylindrical hollow body is arranged in the outlet opening 17 as an axially movable slide or valve means 37. The cylindrical hollow body axially movable slide or valve 37 is closed on the container side by a frontal wall 38 sealing the outlet opening 17 in the closing position. The frontal wall 38 comprises a recess extending into the interior of the hollow cylinder 37 forming a conical guiding body 39. On the level of the conical guiding body two openings 40, 41 are provided in the lateral wall of the hollow cylinder 37.

Furthermore, the hollow cylinder 37 comprises a circumferential locking projection 42 arranged on the periphery. In the closing position of the hollow cylinder 37 represented in FIG. 3, the locking projection 42 abuts on an area of a connection piece 43 directed to the outside. The connection piece 43 is arranged coaxially to the outlet opening 17 on the cover 11. It serves to guide the hollow cylinder 37 and covers the openings 40, 41 in the closing position.

A cap 44 enclosing the hollow cylinder 37 is stuck over the connection piece 43, the interior side of the cap 44 abutting on the outside of the connection piece 43. For the position of the cap 44 being determined exactly and the cap 44 not being able to be moved further into the direction of the cover, the connection piece 43 comprises a circumferential step 45 the lower edge 46 of the cap 44 abuts on. Furthermore, the cap 44 comprises ribs 47, 48 projecting into the hollow cylinder. The ribs 47, 48, which can be supplemented by additional ribs arranged in the shape of a star, serve to position the cap 44 onto the hollow cylinder 37 in an exact manner so that the hollow cylinder 37 is not pushed into the container 10 when the cap 44 is put on. Thus, the cap 44 encloses the hollow cylinder 37 and seals the cover 11 against the connection piece 33.

If a tube connected to a suction source is put on the connection piece 23 of the suction opening 15 to operate the suction device, the suction source produces a low pressure in the container 10 and in the bag 14. Because of the low pressure, a force directed downwards in FIG. 3 is applied to the hollow cylinder 37. In this manner, the hollow cylinder 37 in FIG. 3 can be displaced slightly downwards until a small gap is formed between the frontal wall 38 and the sealing area of the connection piece 43. Because of this gap, a low pressure is also formed in the hollow cylinder 37 so that the same pressure is present in the hollow cylinder 37 and in the bag 14. As the cap 44 is sealingly set on the connection piece 43 and encloses the hollow cylinder 37, the same low pressure is also present in the cap 44. Thus, it is avoided that the hollow cylinder 37 is pulled into the container 10 because of the low pressure present in the bag 14. As the hollow cylinder 37 is returned to the closing position because of the circumferential locking projection 42 of the hollow cylinder 37 after the pressure has been equalized, the hollow cylinder 37 is always in the closing position during the operation of the suction device.

As soon as the bag 14 is full or has to be emptied for some other reason, the suction device is switched off, and the tubes connected to the inlet and suction openings, respectively, are pulled off from the connection pieces 25 and 23, respectively. To avoid any contact with body fluids when pulling off the patient tube, the free end of the patient tube can also be put onto the connection piece 23 of the suction opening. As soon as the low pressure in the bag 14 is relaxed, the hollow cylinder 37 is returned to its closing position by the locking projection 42, and the container 10 can be transported to the faeces room without any risk, for example to evacuate the body fluids collected in the bag 14.

If the bag is filled with body fluid from a patient with a notifiable disease, the connection pieces 23, 25 and the hollow cylinder 37 are closed by means of the caps 24, 26 and 44 so that no fluid can be spilled during transport. Then the entire container is disposed of by wet combustion.

To empty the bag 14, the cap is removed from the connection piece 43. The hollow cylinder slide or valve means continues to be in the closing position so that the container is sealed tightly. Then the hollow cylinder 37 as shown in FIG. 4 is pushed into the container 10 for opening. For this purpose, the suction device can be supported on the container 10 or on the bag 14, i. e. with a sufficient safety distance to the pouring opening, and can be pressed to the bottom of the pouring basin with the cover 11 directed downwards. The hollow cylinder 37 can also be pushed in when the cover 11 is directed upwards by means of any object. The hollow cylinder 37 can be pushed into the container 10 until a projection provided on an end of the hollow cylinder 37 turned away from the container abuts on the upper side of the connection piece 43. Because of the conical shape of the guiding body 39, the fluid does not get into the hollow cylinder 37 immediately, even when the slide 37 is immersed in fluid when being pressed in, so that a contact of the personnel with fluid which might be contaminated is avoided. To pour out the fluid present in the bag 14, the container 10 now just has to be tilted so that the fluid can flow into the hollow cylinder 37 through the openings 40, 41 therein and can be poured out through a pouring opening 52 of the hollow cylinder 37. In this context, the container can be supported on the side opposite the cover 11 so that the contact with the body fluid is avoided further. As the connection pieces 23, 25 terminate on the same level as the hollow cylinder 37 in the opened position, the suction device can just be placed into a reception trough for emptying, with the outlet opening directed downwards. For the fluid to flow off, the container then just has to be displaced laterally so that the outlet opening of the cover 11 is positioned above the drain opening of the pouring basin.

For emptying the bag 14, the cover 11 can also be taken off the container 10 by means of a tab 53. By lifting the cover 11, the bag 14, which is fixedly connected to the cylindrical projection 12 of the cover via the supporting ring 13, is pulled out of the container 10. For transporting, the bag 14 comprises one or multiple supporting straps, which are not represented, on the bottom side opposite the cover 11, whereon the bag can be supported with the cover 11 directed downwards. As the frontal wall 38 of the hollow cylinder 37 seals the outlet opening 17 even when the cover 11 is directed downwards, the cap 44 can be drawn off the connection piece 43 even in this position, without the personnel coming into contact with body fluid. The hollow cylinder 37 is pressed into the bag 14 by the frontal side 54 of the hollow cylinder 37 turned away from the cover 11 being touched down momentarily, for example on the bottom of the reception trough. The connection piece 43 comprises a chamfer 55 locking on the locking projection 42 in an open position so that the hollow cylinder 37 is not pushed back into the closing position when pouring.

If the bag 14 is not emptied, for example for security reasons, the bag 14 can be disposed of together with the cover 11. The container 10, however, can be reused.

Figure 5:
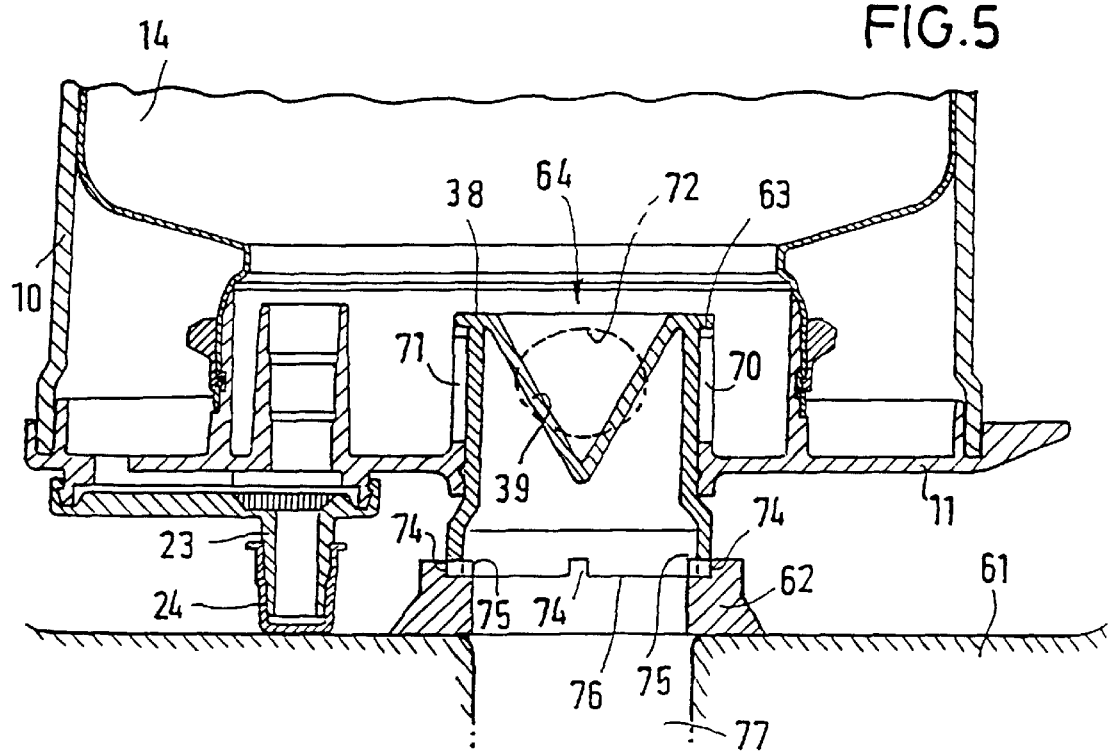
FIG. 5 is a longitudinal cross section of the suction device with a rotatable slide with the outlet opening being closed.
Figure 6:
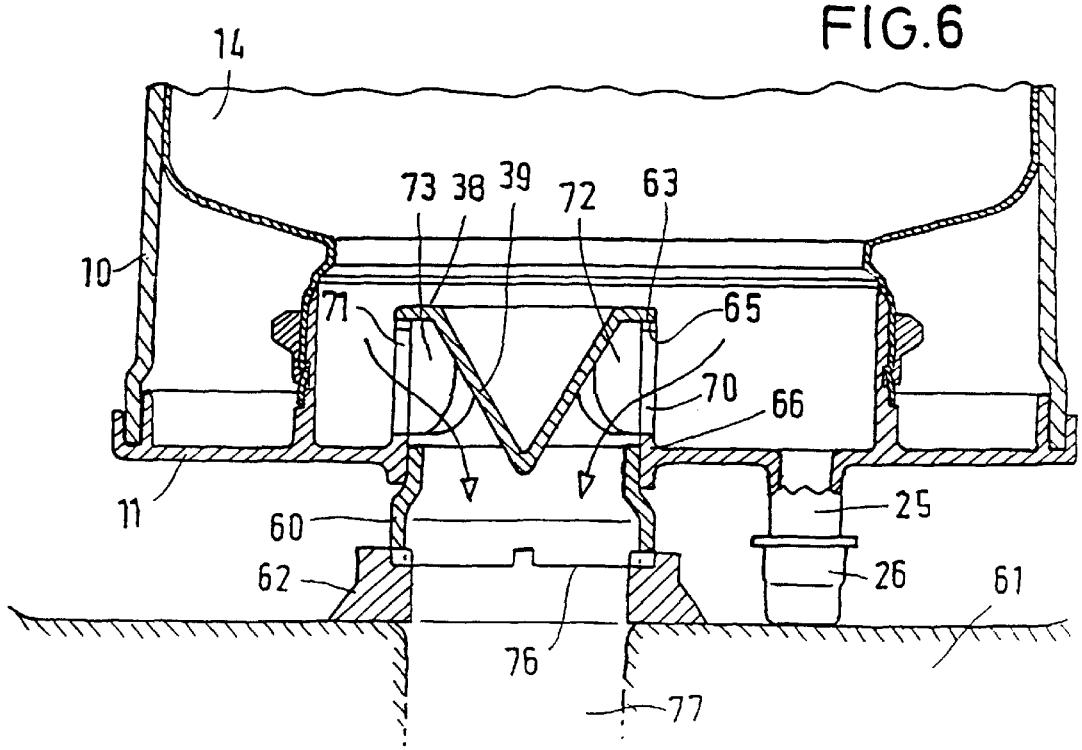
FIG. 6 is a longitudinal cross section of the suction device with a rotatable slide with the outlet opening being opened.

In FIGS. 5 and 6, an embodiment with a rotatable slide 60 is represented. With the exception of the function of the slide, all the connections and functions correspond to the embodiment described with respect to FIGS. 1 to 4. The container 10 is represented in FIGS. 5 and 6 upside down or with the cover 11 directed downwards. The suction device stands on the bottom 61 of a basin in which the closure cap 24 of the connection piece 23 (FIG. 5) and the closure cap 26 of the connection piece 25 (FIG. 6) rest upon the bottom 61 of the basin and the hollow cylinder rotatable slide or rotatable valve means 60 rests upon an opening aid 62.

On the side of the container, the hollow cylinder 60 is closed by a frontal wall 63 sealing the outlet opening of the suction device in the closed position represented in FIG. 5. The frontal wall 63 abuts on a frontal side or seripherad free edge or wall 65 of a cylindrical projection 66 of the cover 11.

The cylindrical projection 66 comprises two openings 70, 71 on the circumference. In the closing position (FIG. 5), the rotatable hollow cylinder 60 is arranged with respect to the cylindrical projection 66 such that the openings 70, 71 are closed by the cylinder wall 66 of the hollow cylinder 60.

For opening, the hollow cylinder 60 has to be turned by 90° relative to the cylindrical projection or wall 66 so that openings 72, 73 of the hollow cylinder 60 align with the openings 70, 71 of the cylindrical projection 66 (FIG. 6). For this purpose, the cylinder 60 is connected to an opening aid 62 by recesses 74 of the hollow cylinder 60 engaging corresponding projections 75 of the opening aid 62. As the opening aid 62 is connected firmly to the bottom 61 of the basin, the hollow cylinder 60 is unrotatably supported by the opening aid 62. For opening, the container 10 is now rotated by 90° from the closing position represented in FIG. 5 to the opening position represented in FIG. 6. In the opening position, the fluid flows out of the bag 14 through the openings 70, 71 of the cylindrical projection 66, through the openings 72, 73 of the hollow cylinder 60 and through an outlet opening 76 of the hollow cylinder 60 into a drain 77 provided in the bottom 61 of the basin. For this purpose, the opening aid 62 is arranged above the drain 77. To avoid an undesired rotation of the hollow cylinder 60 from the closing position, locking projections or the like, which are not represented, can be provided.

Figure 7:
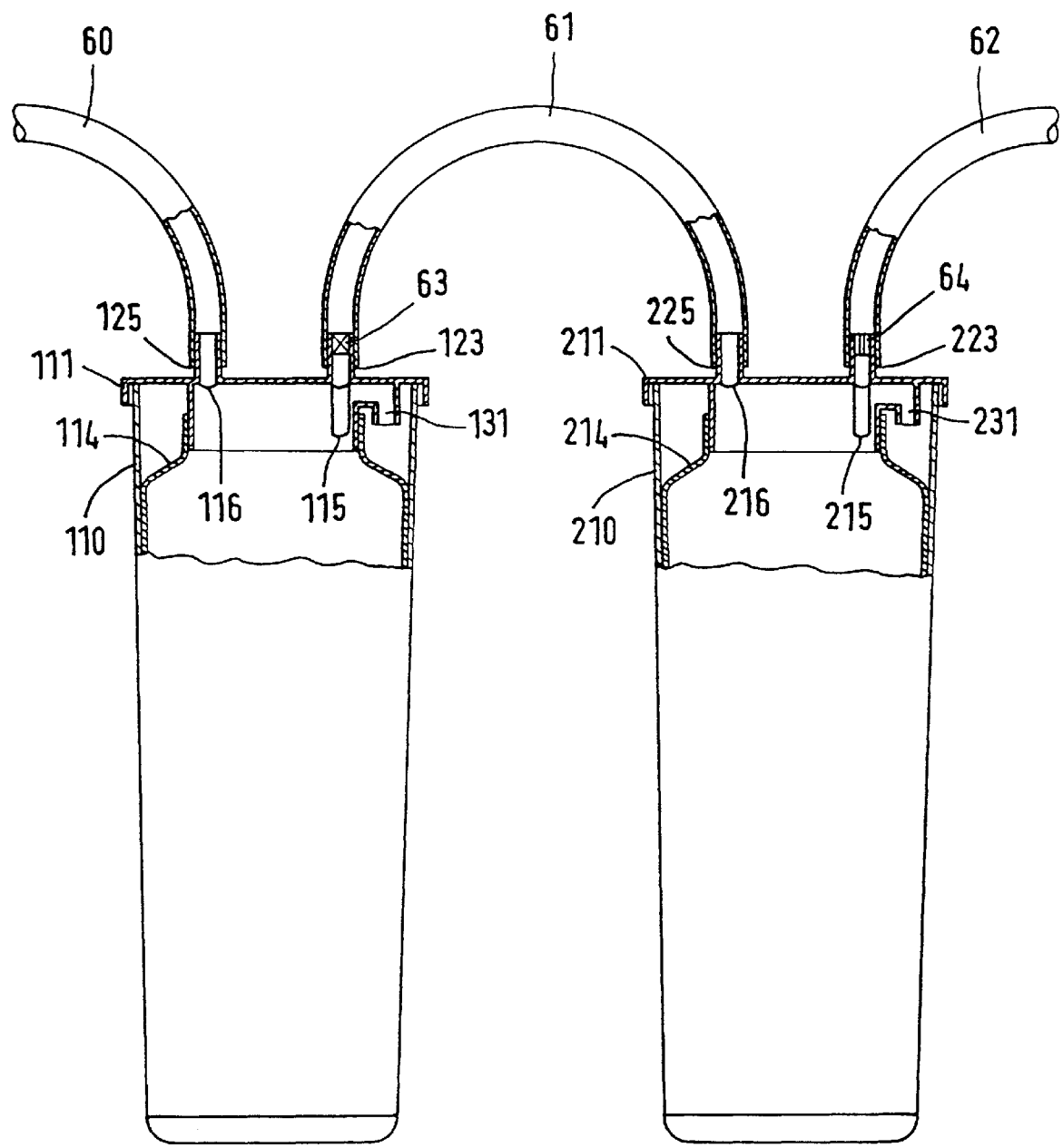
FIG. 7 is an arrangement of two suction devices connected in series.

FIG. 7 shows an arrangement of two suction devices connected in series as they are described with respect to FIGS. 1 to 4 or 5 and 6. For reasons of clarity, the drain is not represented.

A connection piece 125 of an inlet opening 116 of the first container 110 is connected to a tube 60. The tube 60 is connected to a patient. A connection piece 123 of a suction opening 115 is connected to a connection piece 225 of an inlet opening 216 of a second container 210 by means of a tube 61. A connection piece 223 of a suction opening 215 is connected to a suction source via a tube 62.

The suction openings 115, 215 each comprise a branching 131, 231 in the cover 111, 211, which branchings are not connected to the bags 114 and 214, respectively, but are each connected to the container 110, 210. Thus, during operation, a low pressure is produced by the suction source in the bag 214 as well as, via the branching 231, in the container 210. Because of the connection of the two containers 210, 110, a low pressure is also produced in a bag 114 and in the container 110 via a branching 131. After the production of sufficient low pressure, body fluid is drawn off via the tube 60. The body fluid drawn off gets into the bag 114. As soon as the bag 114 is filled, the body fluid in the bag 114 is transported into the bag 214 via the tube 61. The connection piece 115 projects into the bag 114 so that the fluid level does not rise above this level and the bag 214 is filled via the tube 61. To keep the body fluid from flowing back out of the tube 61 into the bag 114, a back pressure valve 63 is provided in the connection piece 123. In the connection piece 222 of the second container 210, a hydrophobic filter 64 is provided according to the suction device described with respect to FIGS. 1 to 4. By means of the hydrophobic filter 64, it is ensured that no fluid gets into the tube 62 and thus to the suction source when the bag 214 is filled.

In the manner described above, a larger number of suction devices can also be arranged in series. In this case, with the exception of the last container connected to the suction device, a back pressure valve is arranged in each connection piece of the suction openings, and in the last connection piece of the container, a hydrophobic filter is arranged.

What is claimed is:

1. A suction device for collecting body fluid comprising a container (10), a flexible bag (14) within the container (10), a cover (11) closing at least an upper end portion (12) of the flexible bag (14); said cover (11) including means (15) for defining a suction opening with respect to said flexible bag and means (17) for defining a fluid inlet/outlet with respect to said flexible bag; valve means (37, 60) exteriorly manipulatable and movably disposed in said fluid inlet/outlet means (17) for selectively opening and closing said fluid inlet/outlet means (17), said valve means (37, 60) including a first wall portion defining at least one opening (16) for placing an interior of said flexible bag (14) into fluid communication with the exterior through said fluid inlet/outlet means (17) in a first open position of said valve means (37, 60), and said valve means (37, 60) further including at least a second wall portion for closing the interior of said bag (14) to fluid communication with the exterior through said fluid inlet/outlet means (17) in a second closed position of said valve means (37).

2. The suction device as defined in claim 1 wherein said valve means (37) is axially movable between said first open position and said second closed position and vice versa.

3. The suction device as defined in claim 1 wherein said valve means (60) is rotatably movable between said first open position and said second closed position and vice versa.

4. The suction device as defined in claim 1 wherein said valve means (37, 60) includes an outermost peripheral edge portion (generally 52, 76) which in said second closed position projects substantially beyond an outer surface of said cover (11) and said fluid inlet/outlet means (17) whereby said outermost peripheral edge portion (generally 52, 76) can be readily manipulated to move said valve means (37, 60) between the first open position and the second closed position and vice versa.

5. The suction device as defined in claim 1 wherein said valve means (37, 60) includes an outermost peripheral edge portion (generally 52, 76) which in said second closed position projects substantially beyond an outer surface of said cover (11) and said fluid inlet/outlet means (17) whereby said outermost peripheral edge portion (generally 52, 76) can be readily manipulated to axially slide said valve means (37) between the first open position and the second closed position and vice versa.

6. The suction device as defined in claim 1 wherein said valve means (37, 60) includes an outermost peripheral edge portion (generally 52, 76) which in said second closed position projects substantially beyond an outer surface of said cover (11) and said fluid inlet/outlet means (17) whereby said outermost peripheral edge portion (generally 52, 76) can be readily manipulated to rotate said valve means (60) between the first open position and the second closed position and vice versa.

7. The suction device as defined in claim 1 wherein said valve means (37, 60) includes an outermost peripheral edge portion (generally 52, 76) which in said second closed position projects substantially beyond an outer surface of said cover (11) and said fluid inlet/outlet means (17) whereby said outermost peripheral edge portion (generally 52, 76) can be readily manipulated to rotate said valve means (60) between the first open position and the second closed position and vice versa, and means (74) for cooperating with an opening device when at least one of the container (10) and the flexible bag (14) is upside down to facilitate the rotation of said valve means (60).

8. The suction device as defined in claim 1 wherein said valve means (37, 60) includes an outermost peripheral edge portion (generally 52, 76) which in said second closed position projects substantially beyond an outer surface of said cover (11) and said fluid inlet/outlet means (17) whereby said outermost peripheral edge portion (generally 52, 76) can be readily manipulated to rotate said valve means (60) between the first open position and the second closed position and vice versa, and means (74) in the form of at least one notch for cooperating with an opening device when at least one of the container (10) and the flexible bag (14) is upside down to facilitate the rotation of said valve means (60).

9. The suction device as defined in claim 1 wherein said valve means (37) is axially pushed into said second closed position in a direction toward the interior of said flexible bag (14) to move the valve means (37) to the second closed position.

10. The suction device as defined in claim 1 wherein said valve means (37, 60) includes means (39) for guiding fluid flow into and out of said flexible bag (14).

11. The suction device as defined in claim 1 wherein said valve means (37, 60) includes means (39) for laterally guiding fluid flow into and out of said flexible bag (14).

12. The suction device as defined in claim 1 wherein said valve means (37, 60) is a substantially hollow body defined by a wall including said first and second wall portions, and said first and second wall portions are in circumferential spaced relationship to each other.

13. The suction device as defined in claim 1 wherein said valve means (37, 60) is a substantially hollow body defined by a wall in which said at least one opening (16) includes at least one opening (40, 41; 72, 73) in said first wall portion.

14. The suction device as defined in claim 1 wherein said valve means (37, 60) is a substantially hollow cylindrical body defined by a wall including said first and second wall portions, and said first and second wall portions are in circumferential spaced relationship to each other.

15. The suction device as defined in claim 1 wherein said valve means (37, 60) is a substantially hollow cylindrical body defined by a wall in which said at least one opening (16) includes at least one opening (40, 41; 72, 73) in said first wall portion.

16. The suction device as defined in claim 1 wherein said valve means (37, 60) includes means (39) for guiding fluid flow into and out of said flexible bag (14), and said fluid flow guiding means (39) is a substantially conical wall portion.

17. The suction device as defined in claim 1 wherein said valve means (37, 60) includes means (39) for guiding fluid flow into and out of said flexible bag (14), and said fluid flow guiding means (39) is a substantially conical wall portion projecting in a direction away from an interior of said flexible bag (14).

18. The suction device as defined in claim 1 wherein said valve means (37, 60) and said fluid inlet/outlet defining means (17) are each defined in part by a cylindrical wall, and said cylindrical walls are in substantially telescopic relationship to each other.

19. The suction device as defined in claim 1 wherein said valve means (37, 60) and said fluid inlet/outlet defining means (17) are each defined in part by a cylindrical wall, and said cylindrical walls are in substantially telescopic rotatable relationship to each other.

20. The suction device as defined in claim 1 wherein said valve means (37, 60) and said fluid inlet/outlet defining means (17) are defined in part by a cylindrical wall, and said cylindrical walls are in substantially telescopic axially sliding relationship to each other.

21. The suction device as defined in claim 1 wherein said valve means (37, 60) and said fluid inlet/outlet defining means (17) are defined in part by a cylindrical wall, said cylindrical walls are in substantially telescopic relationship to each other, and said valve means at least one opening (16) is a lateral opening (40 or 41; 72 or 73) in said valve means cylindrical wall.

22. The suction device as defined in claim 1 wherein said valve means (37, 60) and said fluid inlet/outlet defining means (17) are defined in part by a cylindrical wall, said cylindrical walls are in substantially telescopic relationship to each other, said valve means at least one opening (16) is a lateral opening (40 or 41; 72 or 73) in said valve means cylindrical wall, and said fluid inlet/outlet means cylindrical wall includes at least one opening (70, 71) adapted to register with said at least one opening (72, 73) of said valve means cylindrical wall.

23. The suction device as defined in claim 1 wherein said valve means (37, 60) and said fluid inlet/outlet defining means (17) are defined in part by a cylindrical wall, said cylindrical walls are in substantially telescopic relationship to each other, said valve means at least one opening (16) is a lateral opening (40 or 41; 72 or 73) in said valve means cylindrical wall, said fluid inlet/outlet means cylindrical wall includes at least one opening (70, 71) adapted to register with said at least one opening (72, 73) of said valve means cylindrical wall, and said valve means cylindrical wall includes a conical wall portion projecting in a direction away from an interior of said flexible bag (14) for directing fluid laterally through said openings.

24. The suction device as defined in claim 2 wherein said valve means (37, 60) includes an outermost peripheral edge portion (generally 52, 76) which in said second closed position projects substantially beyond an outer surface of said cover (11) and said fluid inlet/outlet means (17) whereby said outermost peripheral edge portion (generally 52, 76) can be readily manipulated to move said valve means (37, 60) between the first open position and the second closed position and vice versa.

25. The suction device as defined in claim 2 wherein said valve means (37, 60) includes an outermost peripheral edge portion (generally 52, 76) which in said second closed position projects substantially beyond an outer surface of said cover (11) and said fluid inlet/outlet means (17) whereby said outermost peripheral edge portion (generally 52, 76) can be readily manipulated to axially slide said valve means (37) between the first open position and the second closed position and vice versa.

26. The suction device as defined in claim 2 wherein said valve means (37) is axially pushed into said second closed position in a direction toward the interior of said flexible bag (14) to move the valve means (37) to the second closed position.

27. The suction device as defined in claim 2 wherein said valve means (37, 60) includes means (39) for guiding fluid flow into and out of said flexible bag (14).

28. The suction device as defined in claim 2 wherein said valve means (37, 60) and said fluid inlet/outlet defining means (17) are defined in part by a cylindrical wall, said cylindrical walls are in substantially telescopic relationship to each other, said valve means at least one opening (16) is a lateral opening (40 or 41; 72 or 73) in said valve means cylindrical wall, and said fluid inlet/outlet means cylindrical wall includes at least one opening (70, 71) adapted to register with said at least one opening (72, 73) of said valve means cylindrical wall.

29. The suction device as defined in claim 2 wherein said valve means (37, 60) includes an outermost peripheral edge portion (generally 52, 76) which in said second closed position projects substantially beyond an outer surface of said cover (11) and said fluid inlet/outlet means (17) whereby said outermost peripheral edge portion (generally 52, 76) can be readily manipulated to rotate said valve means (60) between the first open position and the second closed position and vice versa, and means (74) for cooperating with an opening device when at least one of the container (10) and the flexible bag (14) is upside down to facilitate the rotation of said valve means (60).

30. The suction device as defined in claim 3 wherein said valve means (37, 60) includes an outermost peripheral edge portion (generally 52, 76) which in said second closed position projects substantially beyond an outer surface of said cover (11) and said fluid inlet/outlet means (17) whereby said outermost peripheral edge portion (generally 52, 76) can be readily manipulated to move said valve means (37, 60) between the first open position and the second closed position and vice versa.

31. The suction device as defined in claim 3 wherein said valve means (37, 60) includes an outermost peripheral edge portion (generally 52, 76) which in said second closed position projects substantially beyond an outer surface of said cover (11) and said fluid inlet/outlet means (17) whereby said outermost peripheral edge portion (generally 52, 76) can be readily manipulated to axially slide said valve means (37) between the first open position and the second closed position and vice versa.

32. The suction device as defined in claim 3 wherein said valve means (37, 60) includes an outermost peripheral edge portion (generally 52, 76) which in said second closed position projects substantially beyond an outer surface of said cover (11) and said fluid inlet/outlet means (17) whereby said outermost peripheral edge portion (generally 52, 76) can be readily manipulated to rotate said valve means (60) between the first open position and the second closed position and vice versa, and means (74) for cooperating with an opening device when at least one of the container (10) and the flexible bag (3) is upside down to facilitate the rotation of said valve means (60).

33. The suction device as defined in claim 3 wherein said valve means (37, 60) includes an outermost peripheral edge portion (generally 52, 76) which in said second closed position projects substantially beyond an outer surface of said cover (11) and said fluid inlet/outlet means (17) whereby said outermost peripheral edge portion (generally 52, 76) can be readily manipulated to rotate said valve means (60) between the first open position and the second closed position and vice versa, and means (74) in the form of at least one notch for cooperating with an opening device when at least one of the container (10) and the flexible bag (14) is upside down to facilitate the rotation of said valve means (60).

34. The suction device as defined in claim 3 wherein said valve means (37, 60) includes means (39) for guiding fluid flow into and out of said flexible bag (14).

35. The suction device as defined in claim 3 wherein said valve means (37, 60) and said fluid inlet/outlet defining means (17) are defined in part by a cylindrical wall, said cylindrical walls are in substantially telescopic relationship to each other, said valve means at least one opening (16) is a lateral opening (40 or 41; 72 or 73) in said valve means cylindrical wall, and said fluid inlet/outlet means cylindrical wall includes at least one opening (70, 71) adapted to register with said at least one opening (72, 73) of said valve means cylindrical wall.

* * * * *